United States Patent
Goto et al.

(10) Patent No.: US 7,550,002 B2
(45) Date of Patent: Jun. 23, 2009

(54) STENT DELIVERY DEVICE

(75) Inventors: Hiroaki Goto, Hachioji (JP); Takaaki Komiya, Hachioji (JP); Yoshimitsu Inoue, Hino (JP)

(73) Assignee: Olympus Corporation, Tokyo (JP)

( * ) Notice: Subject to any disclaimer, the term of this patent is extended or adjusted under 35 U.S.C. 154(b) by 130 days.

(21) Appl. No.: 10/975,881

(22) Filed: Oct. 28, 2004

(65) Prior Publication Data

US 2005/0085891 A1   Apr. 21, 2005

Related U.S. Application Data

(63) Continuation of application No. PCT/JP03/05509, filed on Apr. 30, 2003.

(30) Foreign Application Priority Data

Apr. 30, 2002   (JP) .............................. 2002-128941

(51) Int. Cl.
*A61F 2/06* (2006.01)

(52) U.S. Cl. ..................................... 623/1.12; 623/1.11

(58) Field of Classification Search ................ 623/1.11, 623/1.12, 1.23; 606/108; 600/505, 585; 604/534, 535, 164.09
See application file for complete search history.

(56) References Cited

U.S. PATENT DOCUMENTS

| 5,372,600 | A | * | 12/1994 | Beyar et al. | ................. | 623/1.11 |
| 5,895,391 | A | | 4/1999 | Farnholtz | | |
| 5,921,952 | A | * | 7/1999 | Desmond et al. | ............... | 604/8 |
| 2002/0004676 | A1 | * | 1/2002 | Wallace et al. | ............. | 623/1.12 |
| 2002/0007206 | A1 | * | 1/2002 | Bui et al. | .................... | 623/1.11 |

FOREIGN PATENT DOCUMENTS

| JP | 63-20854 | 2/1988 |
| JP | 5-184684 | 7/1993 |
| JP | 5-220227 | 8/1993 |
| JP | 11-76419 | 3/1999 |
| JP | 2000-152985 | 6/2000 |

* cited by examiner

*Primary Examiner*—(Jackie) Tan-Uyen T. Ho
*Assistant Examiner*—Melanie Tyson
(74) *Attorney, Agent, or Firm*—Scully, Scott, Murphy & Presser, P.C.

(57) ABSTRACT

A stent delivery device is provided with a stent and a pusher tube. A proximal end portion of a linear member is located at a proximal side of the stent. An engagement member is provided at the distal end of the linear member. In response to axial movement of a guide catheter, the engagement member is switched from a first state where it is engaged with the stent to a second state where it is disengaged from the stent.

8 Claims, 5 Drawing Sheets

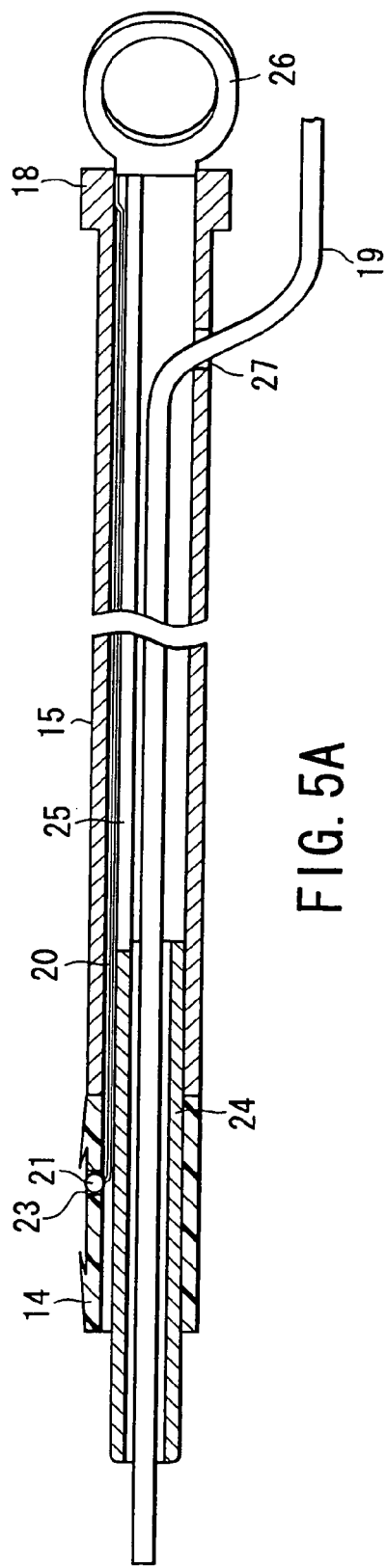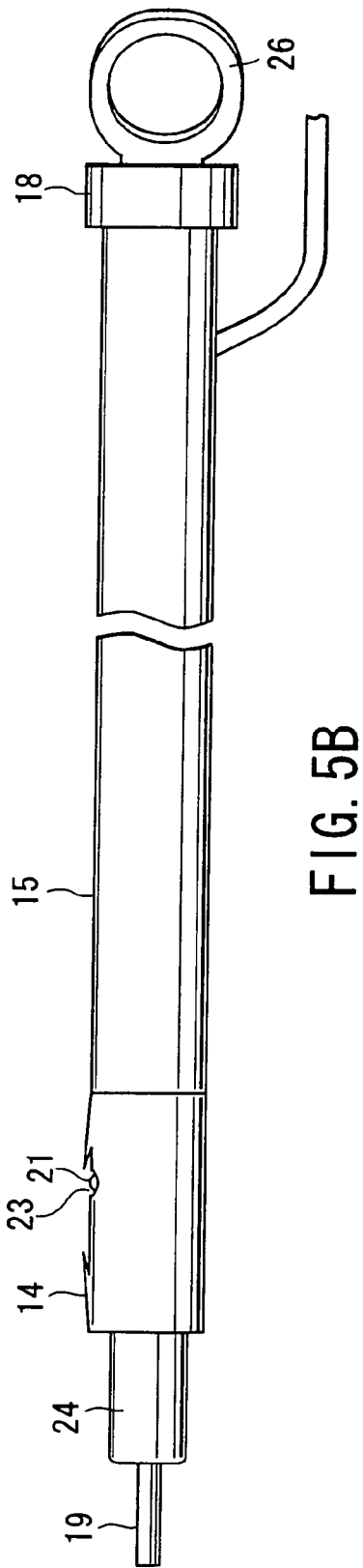
FIG. 5A
FIG. 5B

STENT DELIVERY DEVICE

CROSS REFERENCE TO RELATED APPLICATIONS

This is a Continuation Application of PCT Application No. PCT/JP03/05509, filed Apr. 30, 2003, which was published under PCT Article 21(2) in Japanese.

This application is based upon and claims the benefit of priority from prior Japanese Patent Application No. 2002-128941, filed Apr. 30, 2002, the entire contents of which are incorporated herein by reference.

BACKGROUND OF THE INVENTION

1. Field of the Invention

The present invention relates to a stent delivery device which is used in combination with an endoscope to insert a stent into a body cavity of a patient and place it there.

2. Description of the Related Art

To discharge bile from a bile duct, the following medical treatment is performed. First, the insertion section of an endoscope is inserted into a body cavity. Then, a stent is inserted through a channel of the endoscope and guided to the narrowed area of the bile duct. The stent is placed at the narrowed area of the bile duct. The bile in the bile duct is discharged through the lumen of the stent.

As disclosed in Jpn. UM Appln. KOKAI Publication No. 63-20854, a stent is a comparatively soft hollow tube formed of a macromolecule compound such as poly-ethylene, silicone rubber, or the like. The stent is provided with a flap at each end of the outer wall. With this structure, the stent is prevented from slipping off.

To permit the stent of the above structure to be guided into the body cavity through the use of the endoscope and placed at the narrowed area of the bile duct, the following manual procedures are performed:

As shown in FIG. 10A, an elongated guide wire 3, which is a flexible wire, is inserted through the forceps channel 2 of the insertion section 4 of an endoscope 1. The guide wire 3 is guided to a bile duct 5 together with the insertion section 4 of the endoscope 1. Then, the guide wire 3 is moved forward and inserted through a narrow portion 6 by operating the proximal end of the guide wire 3. As shown in FIG. 10A, a stent 7 is fitted around the proximal end of the guide wire 3 and slid along the guide wire 3. Subsequently, a pusher tube 8 is fitted and slid.

As shown in FIG. 10B, the stent 7 is pushed by means of the pusher tube 8, and the guide wire 3 passed through the narrowed area 6 is used as a guide then. The stent 7 in this state is inserted through the narrowed area 6 and placed there.

U.S. Pat. No. 5,921,952 discloses a drainage catheter delivery system wherein a pusher tube and a stent are coupled together by means of a thread. As will be detailed below, the drainage catheter delivery system is advantageous in that the stent pushed in too much can be pulled back when the pusher tube that is connected to the stent by means of the thread is pulled back.

In the drainage catheter delivery system, an insertion hole in which the thread is inserted is formed at the distal end portion of the pusher tube. The stent is provided with a hole defined by flaps. A thread (a suture), jointed with a guide wire, goes through the hole of the stent and is inserted through the insertion hole of the pusher tube and fastened. In this manner, the stent and the pusher tube are coupled together.

If the stent is pushed in too much, the pusher tube is moved back, and the stent is pulled by the thread and returned to the original position. When it is desired that the stent be placed at the narrowed area, the stent is first guided to the narrowed area and then the guide wire is pulled back. When the distal end portion of the guide wire is disengaged from the thread, the thread is pulled off the stent. In this manner, the stent and the pusher tube is disconnected.

BRIEF SUMMARY OF THE INVENTION

A stent delivery device embodying the present invention comprises a stent to be placed in the body cavity. The stent has a lumen. A pusher tube, used for moving the stent, is located at a proximal side of the stent. An elongated guide catheter is inserted through both the stent and the pusher tube in such a manner that it can be moved forward and backward. A guide wire can be arranged at least at the distal end of the guide catheter. The stent delivery device of the present invention comprises a linear member. A proximal end of this linear member is located at the proximal side of the stent. An engagement member is provided at the distal end of the linear member. By axially moving the guide catheter, the engagement member is switched in state, from the first state where it is engaged with the stent to the second state where it is disengaged from the stent.

The stent of the present invention preferably has an engagement depression formed in the inner wall thereof and engageable with the engagement member. In the first state, the engagement member is in engagement with the engagement depression and the circumferential wall of the guide catheter inserted in the stent.

The proximal end portion of the linear member of the present invention is preferably fixed to the pusher tube.

In the first state, the engagement member of the present invention is preferably in engagement with both the distal end face of the stent and the circumferential wall of the guide catheter projected from the distal end portion of the stent.

The circumferential wall of the guide catheter of the present invention preferably has an opening into which the engagement member puts. When the engagement member puts into the opening, the second state is established.

The stent of the present invention preferably has an engagement hole with which the engagement member is engageable. In the first state, the engagement member is in engagement with the engagement hole and the circumferential wall of the guide catheter inserted in the stent.

The guide catheter of the present invention is preferably being located on the distal end side of the pusher tube. The proximal end portion of the guide catheter is connected to the distal end portion of a pull wire inserted in the pusher tube. Inside the pusher tube, the pull wire can be moved forward or backward.

The stent delivery device of the present invention comprises a stent, which is to be inserted into a body cavity and placed there. The stent has a lumen. A pusher tube, used for moving the stent, is located at a proximal side of the stent. An elongated guide member is inserted through the stent and the pusher tube in such a manner that it can be moved forward and backward. The stent delivery device of the present invention comprises a linear member. A proximal end of this linear member is located at the proximal side of the stent. An engagement member is provided at the distal end of the linear member. By axially moving the guide member, the engagement member is switched from the first state where it is engaged with the stent to the second state where it is disengaged from the stent.

In the first state, the engagement member of the present invention is preferably in engagement with the circumferential wall of the guide member inserted in the stent and the inner surface of the stent. At the time, the distal end portion of the engagement member is located on the distal end side of the stent. In addition, the proximal end portion of the engagement member is located on the proximal end portion of the stent.

The stent delivery device of the present invention comprises a stent, which is to be inserted into a body cavity and placed there. The stent has a lumen. A pusher tube, used for moving the stent, is located at a proximal side of the stent. A guide catheter is inserted through the stent and the pusher tube in such a manner that it can be rotated on its longitudinal axis. A guide wire can be arranged at least at the distal end of the guide catheter. The stent delivery device of the present invention comprises a linear member. A proximal end of this linear member is located at the proximal side of the stent. An engagement member is provided at the distal end of the linear member. By rotating the guide catheter on its longitudinal axis, the engagement member is switched from the first state where it is engaged with the stent to the second state where it is disengaged from the stent.

BRIEF DESCRIPTION OF THE SEVERAL VIEWS OF THE DRAWING

FIG. 5A is a longitudinal sectional view illustrating the fifth embodiment of the present invention and showing the stent delivery device.

FIG. 5B is a side view showing the stent delivery device of FIG. 5A.

DETAILED DESCRIPTION OF THE INVENTION

Figure 1A:
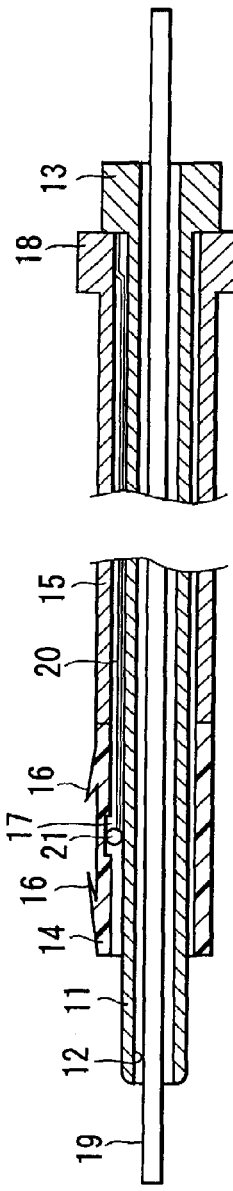
FIG. 1A is a longitudinal sectional view illustrating the first embodiment of the present invention and showing a stent delivery device wherein a stent is in an engagement state.
Figure 1B:
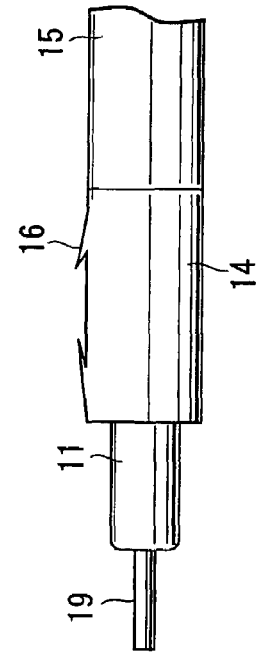
FIG. 1B is a side view showing the distal end portion of the stent delivery device of FIG. 1A.
Figure 1C:
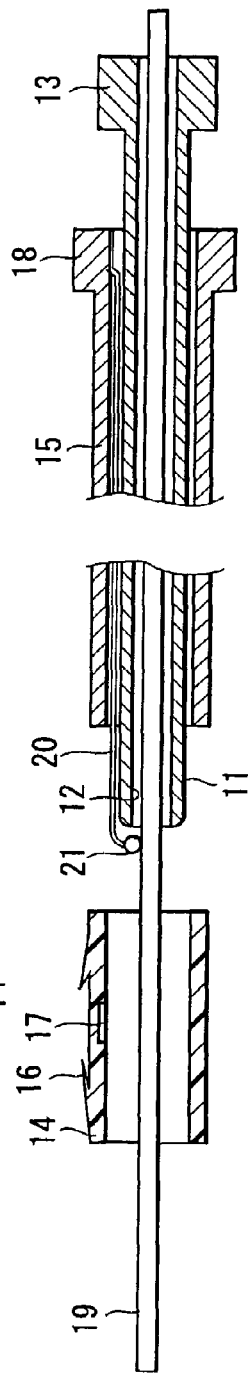
FIG. 1C is a longitudinal sectional view illustrating the first embodiment of the present invention and showing the stent delivery device wherein the stent is not in an engagement state.
Figure 1D:
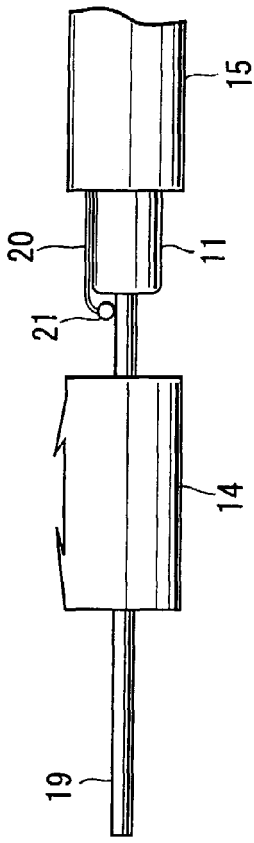
FIG. 1D is a side view showing the distal end portion of the stent delivery device of FIG. 1C.

FIG. 1A is a longitudinal sectional view illustrating the first embodiment of the present invention and showing a stent delivery device wherein a stent is in an engagement state. FIG. 1B is a side view showing the distal end portion of the stent delivery device of FIG. 1A. FIG. 1C is a longitudinal sectional view illustrating the first embodiment of the present invention and showing the stent delivery device wherein the stent is not in an engagement state. FIG. 1D is a side view showing the distal end portion of the stent delivery device of FIG. 1C.

A guide catheter 11 is an elongated guide member which can be inserted into the forceps channel of an endoscope. The guide catheter 11 is made of a synthetic resin material having flexibility, such as fluorocarbon resin or nylon resin. The guide catheter 11 has a lumen 12 throughout the length. A guide catheter cock 13 is at the proximal end of the guide catheter 11.

A stent 14 is provided at the distal end of the guide catheter 11. The stent 14 has a lumen. The guide catheter 11 is inserted in the lumen of the stent 14. A pusher tube 15 is provided on the proximal side of the stent 14. The guide catheter 11 is inserted in the in the lumen of the pusher tube 15.

The stent 14 is a tubular and is comparatively soft. The stent 14 is made of a resin having biocompatibility, such as polyethylene, fluorocarbon resin, nylon resin, thermoplastic elastomer, or silicone rubber. The outer circumferential surface of the stent 14 is preferably coated with a hydrophilic lubricating agent. Flaps 16 and 16 opposing each other are formed at the respective end portions of the stent 14, for the purpose of preventing the stent 14 from slipping off. An engagement depression 17 is formed in the inner circumferential surface of the stent 14.

The pusher tube 15 is made of a synthetic resin material having flexibility, such as fluorocarbon resin or nylon resin. A pusher tube cock 18 is at the proximal end of the pusher tube 15.

A guide wire 19 is inserted through the lumen of the guide catheter 11 and extends in the axial direction. A linear member 20 is located between the outer circumferential surface of the guide catheter 11 and the inner circumferential surface of the pusher tube 15. The linear member 20 extends in the axial direction.

The guide wire 19 is an elongated metallic linear, twisted or coil member, or the like. The guide wire 19 is preferably made of a metallic material having super-elasticity, such as an alloy of nickel and titanium. The distal end of the guide wire 19 is tapered. The proximal end of the guide wire 19 is led out of the guide catheter cock 13.

The linear member 20 is made of stainless steel, a nickel, titanium alloy, nylon, liquid crystal polymer, silk, or the like. An engagement member 21 is provided at the distal end of the linear member 20. The engagement member 21 can engage with the engagement depression 17 of the stent 14 or disengage therefrom. The engagement member 21 is a ball-like member made of a metallic material, a ceramic material, thermoplastic resin, or the like. The proximal end of the linear member 20 is fixed to the pusher tube cock 18.

In the state where the guide catheter 11 is inserted in the stent 14, the outer circumferential surface of the guide catheter 11 pushes the engagement member 21 against the engagement depression 17. In other words, the engagement member 21 is in engagement with the engagement depression 17. In this state, the stent 14 can be moved toward the operator by pulling the linear member 20 toward the operator. When the guide catheter 11 is pulled off the stent 14, the engagement member 21 moves out of the engagement depression 17. Accordingly, the engagement member 21 is disengaged.

As can be understood from the above, the only requirement of the engagement member 21 is that it can engage or disengage from the engagement depression 17, of the stent 14. In other words, the engagement member 17 is not limited to the ball-like member described above and may be a cylindrical member, a rectangular block member, or a hook member.

The operation of the first embodiment will be described. In the following description, reference will be made to the case where the stent delivery device having the above structure is guided into a body cavity through an endoscope and where the stent 14 is placed at the narrowed area of the bile duct. As shown in FIGS. 1A and 1B, the pusher tube 15 is fitted around the distal end portion of the guide catheter 11 and slid. Further, the stent 14 is fitted around the distal end portion of the guide catheter 11 and slid. In this case, the engagement member 21, which is at the distal end of the linear member 20 led out of the lumen of the pusher tube 15, is brought into engagement with the engagement depression 17.

The insertion section of the endoscope is inserted into the body cavity and guided to a position in the neighborhood of the bile duct. Then, the guide wire 19 is inserted into the forceps channel of the endoscope. The guide wire 19 is moved forward while being monitored by use of the endoscope and X-rays. The guide wire 19 is moved forward until its distal end comes to the narrowed area of the bile duct.

The guide catheter 11 is fitted around the proximal end portion of the guide wire 19 and slid. At the time, the guide catheter 11 is provided with the stent 14 and the pusher tube 15. The guide catheter 11 is inserted into the forceps channel, using the guide wire as a guide.

The guide catheter 11 is moved forward by manually operating the proximal end portion, and the distal end portion of the guide catheter 11 is pushed out of the distal end section of the endoscope. Further, the distal end portion of the guide catheter 11 is inserted into the narrowed area. By pushing in the pusher tube 15, the stent 14 is moved along the guide catheter 11 and inserted into the narrowed area. In this state, the distal end of the stent 14 is located closer to the operator than the distal end of the guide catheter 11 is.

If it is found out by X-ray observation or the like that the stent 14 is pushed in too much, the pusher tube 15 is pulled toward the operator. By so doing, the linear member 20 moves the stent 14 back.

Then, the guide catheter 11 is pulled toward the operator. The guide catheter 11 is pulled relative to the stent 14, without operating the guide wire 19. By so doing, the distal end portion of the guide catheter 11 comes out of the lumen of the stent 14. As a result, the engagement member 21 moves out of the engagement depression 17 of the stent 14, as shown in FIGS. 1C and 1D. Therefore, the linear member 20 and the stent 14 separate from each other. In this manner, the stent 14 is placed at the narrowed area.

At the time, the distal end of the guide wire 19 is located at the narrowed area. Therefore, the guide wire 19 remains inserted through the narrowed area.

The structure described above is advantageous as follows. In the present embodiment, the stent 14 is moved forward by the pusher tube 15, for the placement of the stent 14. At the time, the guide catheter 11 is inserted through the coupling section where the stent 14 and the pusher tube 15 are coupled together. This structure provides a high degree of bending strength for the coupling section where the stent 14 and the pusher tube 15 are coupled together. Even if the path along which the stent 14 is moved forward is curved largely, the stent 14 and the pusher tube 15 do not buckle. Therefore, the stent 14 can be moved smoothly.

When the stent 14 is placed, the engagement member 21 is in engagement with it. It should be also noted that the engagement member 21 is connected to the distal end portion of the linear member 20, and that the proximal end portion of the linear member 20 is fixed to the pusher tube 15. Therefore, if the stent 14 is pushed in too much, it can be moved back by pulling the pusher tube 15 toward the operator.

For the placement of the stent 14, the guide catheter 11 is pulled toward the operator relative to the stent. At the time, the guide wire 19 inserted through the guide catheter 11 is kept as it is. After the stent 14 is placed, the distal end portion of the guide wire 19 remains inserted through the narrowed area. Therefore, the next operation can be performed using the wire guide 19 as a guide.

Figure 2:
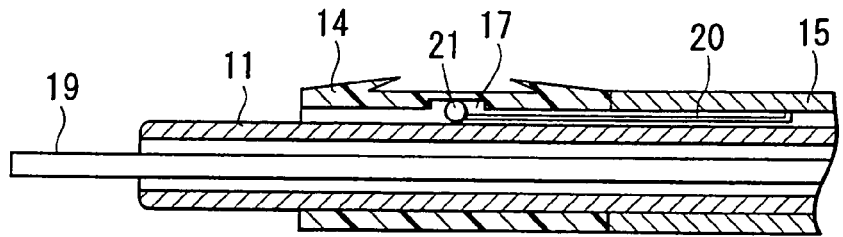
FIG. 2 is a longitudinal sectional view illustrating the second embodiment of the present invention and showing the distal end portion of a stent delivery device.

FIG. 2 is a longitudinal sectional view illustrating the second embodiment of the present invention and showing the distal end portion of a stent delivery device. In the description below, the same reference numerals as used in connection with the first embodiment denote corresponding or similar structural elements, and a repeated description of such structural elements will be omitted.

In the present embodiment, the proximal end of a linear member 20 is coupled to the inner surface of the distal end portion of a pusher tube 15. The second embodiment operates in a similar manner to that of the first embodiment and is advantageous in that the linear member 20 is comparatively short. Because of this simple structure, the second embodiment is effective in reducing the costs.

Figure 3:
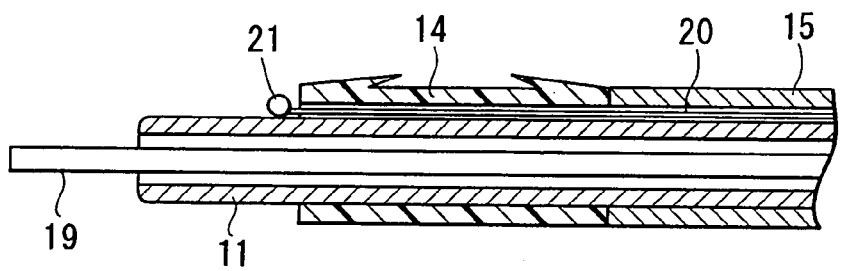
FIG. 3 is a longitudinal sectional view illustrating the third embodiment of the present invention and showing the distal end portion of a stent delivery device.

FIG. 3 is a longitudinal sectional view illustrating the third embodiment of the present invention and showing the distal end portion of a stent delivery device. In the description below, the same reference numerals as used in connection with the first embodiment denote corresponding or similar structural elements, and a repeated description of such structural elements will be omitted.

In the third embodiment, an engagement member 21 at the distal end of a linear member 20 is in engagement with the distal end surface of a stent 14. The third embodiment operates in a similar manner to that of the first embodiment and is advantageous in that the stent 14 need not have an engagement depression 17. Since a conventional stent 14 can be used as it is, cost reduction is possible.

Figure 4A:
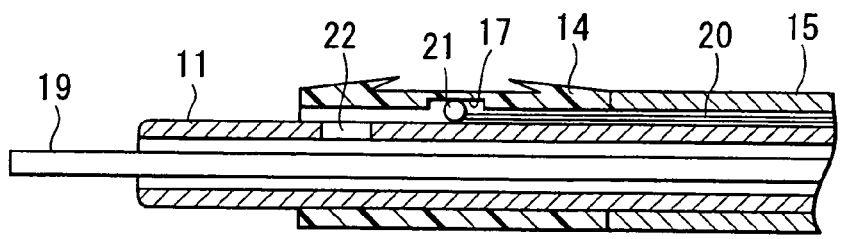
FIG. 4A is a longitudinal sectional view illustrating the fourth embodiment of the present invention and showing the distal end portion of a stent delivery device wherein a stent is in an engagement state.
Figure 4B:
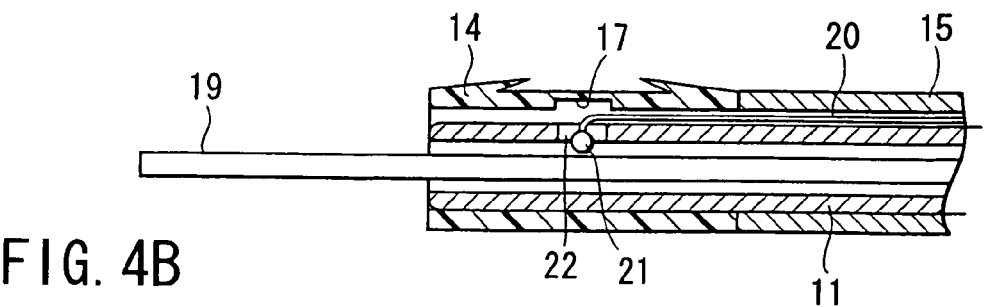
FIG. 4B is a longitudinal sectional view illustrating the fourth embodiment of the present invention and showing the distal end portion of the stent delivery device wherein the stent is not in an engagement state.

FIG. 4A is a longitudinal sectional view illustrating the fourth embodiment of the present invention and showing the distal end portion of a stent delivery device wherein a stent is in an engagement state. FIG. 4B is a longitudinal sectional view illustrating the fourth embodiment of the present invention and showing the distal end portion of the stent delivery device wherein the stent is not in an engagement state.

In the fourth embodiment, a hole 22 is formed in the circumferential wall of the distal end of a guide catheter 11 in such a manner that the hole 22 can be located inside the hollow section of a stent 14. The hole 22 can be opposed to an engagement depression 17. An engagement member 21 can drop into the hole 22.

In the fourth embodiment, the stent is inserted into the narrowed area by pushing a pusher tube 15. If X-ray observation shows that the stent 14 is pushed in too much, the pusher tube 15 is pulled back toward the operator. By so doing, the linear member 20 pulls back the stent 14, and the stent 14 can be positioned accurately at the target position.

Then, the guide catheter 11 is pulled without operating the guide wire 19 and the pusher tube 15. As a result, the hole 22 of the guide catheter 11 comes to the position opposing the engagement depression 17. Thus, the engagement member 21 drops into the hole 22. As shown in FIG. 4B, the engagement member 21 comes out of the engagement depression 17 of the stent 14. In this manner, the linear member 20 and the stent 14 are separated. As a result, the stent 14 is placed at the narrowed area.

According to the fourth embodiment, the guide catheter 11 is pulled slightly toward the operator until the hole 22 comes to the position opposing the engagement member 21. Since the engagement member 21 drops into the hole 22, the linear member 20 and the stent 14 separate from each other. In this manner, the fourth embodiment is improved in operational performance.

FIG. 5A is a longitudinal sectional view illustrating the fifth embodiment of the present invention and showing the stent delivery device. FIG. 5B is a side view showing the stent delivery device of FIG. 5A. In the description below, the same reference numerals as used in connection with the first embodiment denote corresponding or similar structural elements, and a repeated description of such structural elements will be omitted.

An engagement hole 23 is formed in the circumferential wall of a stent 14. An engagement member 21 at the distal end of a linear member 20 is engageable with the engagement hole 23. The proximal end of the linear member 20 is connected to a pusher tube cock 18.

A short guide catheter 24 is inserted in both the stent 14 and the distal end portion of a pusher tube 15, in such a manner that the guide catheter 24 can be moved forward or backward. The proximal end of the guide catheter 24 is connected to the distal end of a pull wire 25. The pull wire 25 extends to the proximal end of the pusher tube 15. The proximal end of the pull wire 25 is coupled to an operation ring 26. A side hole 27 is formed in the pusher tube 15 at a position in the neighborhood of the proximal end. The guide wire 19 is led out through the side hole 27.

According to the fifth embodiment, the stent 14 is inserted into the narrowed area, using the guide catheter 24. If X-ray observation shows that the stent 14 is pushed in too much, the pusher tube 15 is pulled back toward the operator. By so doing, the linear member 20 pulls back the stent 14, and the stent 14 can be positioned accurately at the target position.

Then, the operator takes hold of the operation ring 26 without operating the guide wire 19 and the pusher tube 15. When the pull wire 25 is pulled toward the operator, the guide catheter 24 is pulled back until the distal end of the guide catheter 24 comes to a position which is closer to the operator than the engagement hole 23 is. As a result, the engagement member 21, which has been in engagement with the engagement hole 23 until then, comes out of the engagement hole 23. In this manner, the linear member 20 and the stent 14 are separated. As a result, the stent 14 is placed at the narrowed area.

The fifth embodiment is advantageous in that it does not require a long guide catheter 11. Because of the simple structure, the fifth embodiment is effective in reducing the costs.

Figure 6:
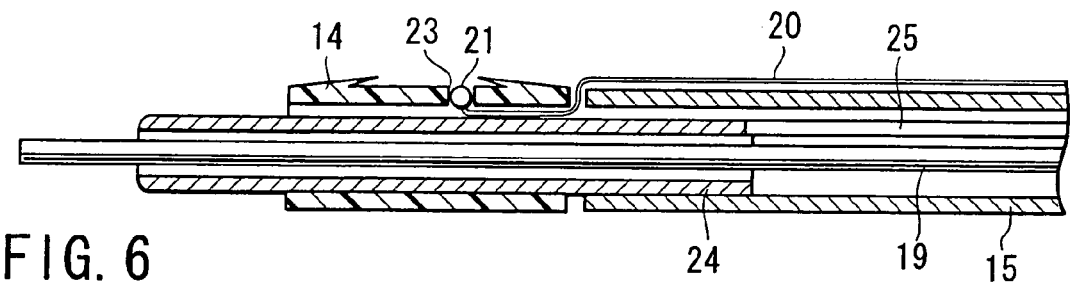
FIG. 6 is a longitudinal sectional view illustrating the sixth embodiment of the present invention and showing the distal end portion of a stent delivery device.

FIG. 6 is a longitudinal sectional view illustrating the sixth embodiment of the present invention and showing the distal end portion of a stent delivery device. In the description below, the same reference numerals as used in connection with the fifth embodiment denote corresponding or similar structural elements, and a repeated description of such structural elements will be omitted.

In the sixth embodiment, a linear member 20 extends along the outer surface of a pusher tube 15, and the distal end of the linear member 20 is inserted into the lumen of a stent 14 after guiding it through the region between the distal end of the pusher tube 15 and the stent 14. An engagement member 21 is engaged with an engagement hole 23. The sixth embodiment operates in a similar manner to that of the fifth embodiment. Since the assembly of the linear member 20 is simple in the sixth embodiment, the assembling operation can be performed with high efficiency.

Figure 7:
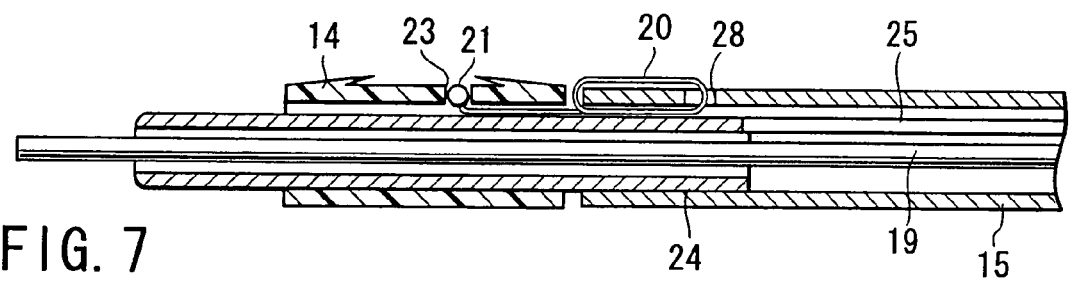
FIG. 7 is a longitudinal sectional view illustrating the seventh embodiment of the present invention and showing the distal end portion of a stent delivery device.

FIG. 7 is a longitudinal sectional view illustrating the seventh embodiment of the present invention and showing the distal end portion of a stent delivery device. In the description below, the same reference numerals as used in connection with the fifth embodiment denote corresponding or similar structural elements, and a repeated description of such structural elements will be omitted.

In the seventh embodiment, a through hole 28 is formed in the side wall of the distal end portion of a pusher tube 15. A linear member 20 is passed through the hole 28 and is then connected to the distal end of the pusher tube 15. The seventh embodiment operates in a similar manner to that of the fifth embodiment and is advantageous in that the linear member 20 is comparatively short. Because of the simple structure, the seventh embodiment is effective in reducing the costs.

Figure 8A:
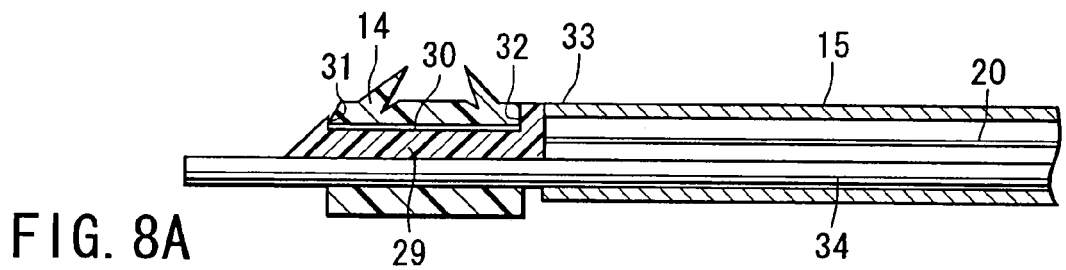
FIG. 8A is a longitudinal sectional view illustrating the eighth embodiment of the present invention and showing the distal end portion of a stent delivery device wherein a stent is in an engagement state.
Figure 8B:
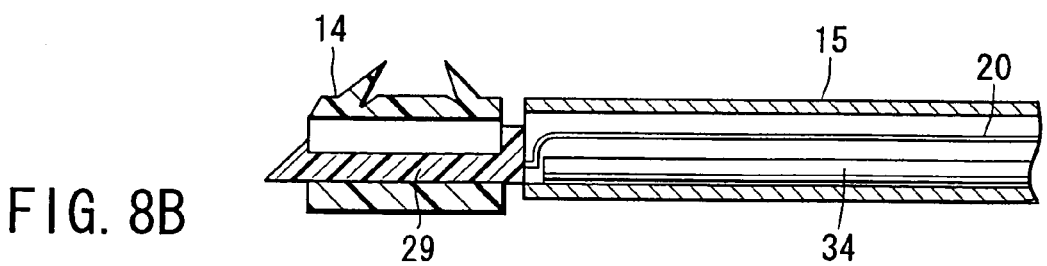
FIG. 8B is a longitudinal sectional view illustrating the eighth embodiment of the present invention and showing the distal end portion of the stent delivery device wherein the stent is not in an engagement state.
Figure 8C:
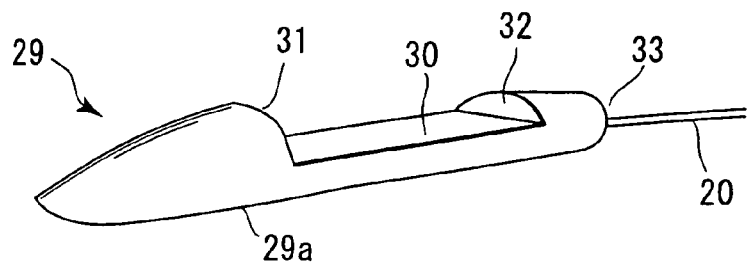
FIG. 8C is a perspective view showing an engagement member employed in the eighth embodiment of the present invention.

FIG. 8A is a longitudinal sectional view illustrating the eighth embodiment of the present invention and showing the distal end portion of a stent delivery device wherein a stent is in an engagement state. FIG. 8B is a longitudinal sectional view illustrating the eighth embodiment of the present invention and showing the distal end portion of the stent delivery device wherein the stent is not in an engagement state. FIG. 8C is a perspective view showing an engagement member employed in the eighth embodiment of the present invention. In the description below, the same reference numerals as used in connection with the first embodiment denote corresponding or similar structural elements, and a repeated description of such structural elements will be omitted.

In the eighth embodiment, the ball-like engagement member 21 used in the first embodiment is replaced with an elongated engagement member 29, as shown in FIGS. 8A, 8B and 8C. Although the guide member of the eighth embodiment is a rod-like member 34, a guide catheter 11 may be used instead.

As shown in FIG. 8C, the engagement member 29 of the eighth embodiment has a depression 30. This depression 30 is formed by cutting out part of the main body 29a of the engagement member 29. A stent 14 has its inner wall portion fitted in the depression 30 along the axial direction. The proximal end 33 of the engagement member 29 is connected to the distal end of a linear member 20.

In the state where the rod-like member 34 is inserted through the stent 14, as shown in FIG. 8A, the engagement member 29 is pushed by the circumferential wall of the rod-like member 34, and the stent 14 is fitted and engaged with the engagement member 29. The distal end portion of the depression 30 holds the distal end portion of the stent 14, and the proximal end portion 32 of the depression 30 holds the proximal end portion of the stent 14. The proximal end 32 of the engagement member 29 is pulled toward the operator by the linear member 20, and pushed against the pusher tube 15.

According to the eighth embodiment, the stent 14 is inserted into the narrowed area by means of the pusher tube 15. If X-ray observation shows that the stent 14 is pushed in too much, the linear member 20 is pulled back toward the operator. At the time, the distal end portion 31 of the engagement member 29 pushes the distal end portion of the stent 14 toward the operator.

After the stent 14 is positioned at the target position, the rod-like member 34 is moved relative to the stent 14 in such a manner that the rod-like member 34 comes closer to the operator. Thereafter, the rod-like member 34 is pulled off the stent 14. Since the engagement member 29 is disengaged from the stent 14, it separates from the stent 14. In this manner, the stent 14 is placed at the target position. Thereafter, the engagement member 29 is received into the pusher tube 15 by pulling the linear member 20 toward the operator.

According to the eighth embodiment, the engagement member 29 is engaged with the stent 14 by fitting the stent 14 in the depression 30. In this state, the engagement member 29 holds both the distal and proximal end portions of the stent 14. Since the engagement member 29 holds both end portions of the stent 14, the stent 14 moves accurately and reliably when it is pushed in or pull out.

The stent 14 need not be worked in a special way, and a conventional stent can be used without any modification. Hence, the manufacturing cost can be reduced.

Figure 9A:
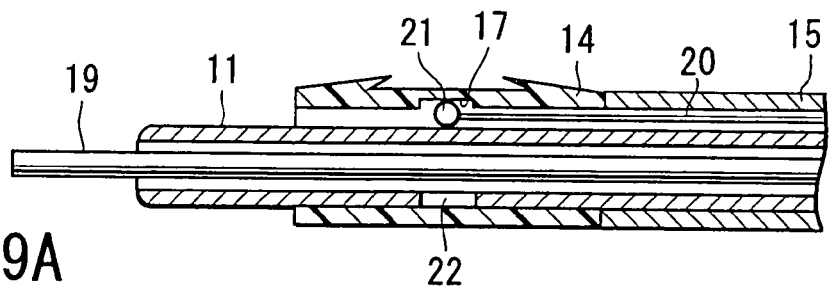
FIG. 9A is a longitudinal sectional view illustrarting the ninth embodiment and showing the distal end portion of a stent delivery device wherein a stent is in an engagement state.
Figure 9B:
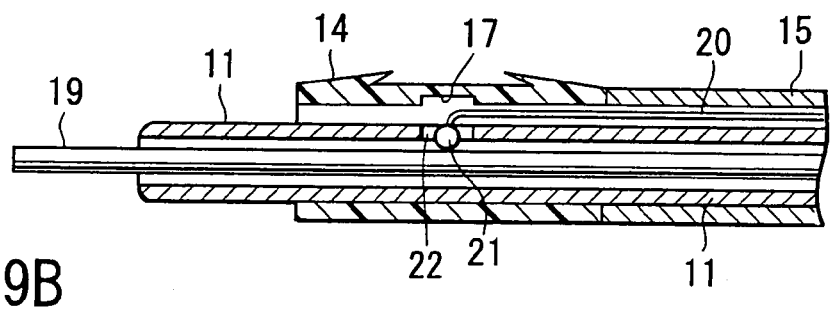
FIG. 9B is a longitudinal sectional view illustrating-the ninth embodiment and showing the distal end portion of the stent delivery device wherein the stent is not in an engagement state.
Figure 10A:
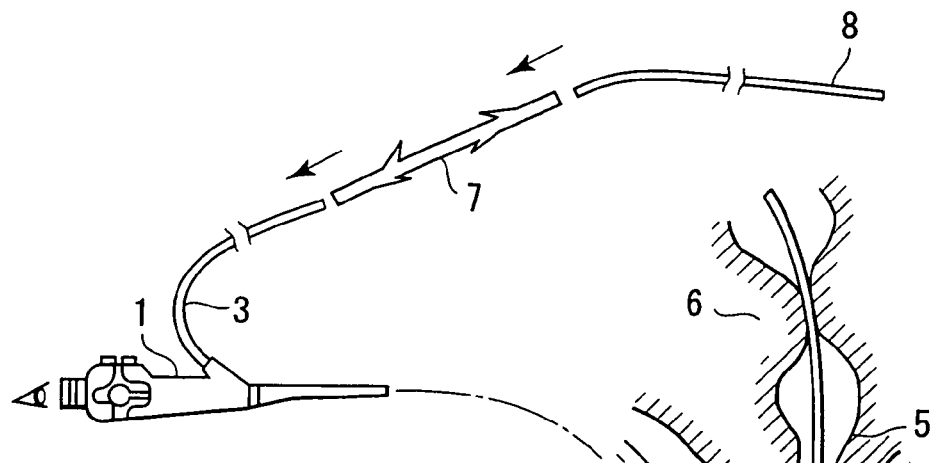
FIG. 10A is an explanatory diagram illustrating the manual operation that is performed when a stent is guided into a body cavity through an endoscope.
Figure 10B:
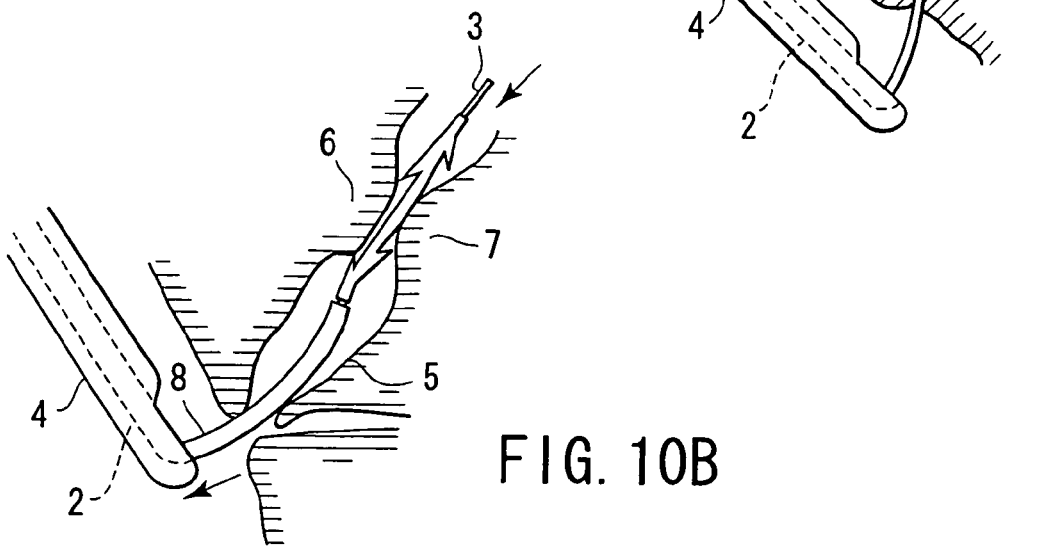
FIG. 10B is an explanatory diagram illustrating the manual operation that is performed to place the stent at the narrowed area of the bile duct after the stent is guided into the body cavity through the endoscope.

FIG. 9A is a longitudinal sectional view illustrating the ninth embodiment and showing the distal end portion of a stent delivery device wherein a stent is in an engagement state. FIG. 9B is a longitudinal sectional view illustrating the ninth embodiment and showing the distal end portion of the stent delivery device wherein the stent is in an engagement state. In the description below, the same reference numerals as used in connection with the fourth embodiment denote similar or corresponding structural elements, and a repeated description of such elements will be omitted herein.

In the ninth embodiment, a guide catheter 11 is inserted through both a stent 14 and a pusher tube 15. The guide catheter 11 can be rotated on its longitudinal axis. An opening 22 is formed in the circumferential wall of the distal end portion of the guide catheter 11 at a position which is inserted in the lumen of the stent 14. An engagement member 21 can drop into the opening 22. The opening 22 is in a plane which is substantially perpendicular to the central axis of the stent 14 and which passes an engagement depression 17.

According to the ninth embodiment, the guide catheter 11 can be rotated on its longitudinal axis without operating the guide wire 19 and the pusher tube 15. As a result of this rotation, the opening 22 of the guide catheter 11 is opposed to the engagement depression 17, and the engagement member 22 drops into the opening 22. As shown in FIG. 9B, the engagement member 20 comes out of the engagement depression 17 of the stent 14. As a result, the linear member 20 and the stent 14 separate from each other. In this manner, the stent 14 is placed at the narrowed area.

In the ninth embodiment, the guide catheter 11, which is in the inside of the stent 14 and the pusher tube 15, is rotatable on its longitudinal axis. In addition, the opening 22 is formed in the circumferential wall of the guide catheter 11, and the engagement member 21 can drop into the opening 22. The opening is in the plane which is substantially perpendicular to the central axis of the stent and which passes the engagement depression 17. With this structure, the engagement member 21 drops into the opening 22 by slightly rotating the guide catheter 11. In this manner, the stent 14 and the engagement member 21 are disengaged from each other. In this manner, the ninth embodiment is improved in operational performance.

The present invention provides a stent delivery device which is used in combination with an endoscope and which enables a stent to be accurately positioned in a body cavity and placed there.

What is claimed is:

1. A stent delivery device comprising:
a stent configured to be placed in a body cavity and including a lumen and an engagement receiving portion;
a pusher tube configured to be located at a proximal side of the stent;
an elongated guide catheter configured to be inserted through the stent and the pusher tube such that the guide catheter is movable in an axial direction of the guide catheter with respect to the stent and the pusher tube, the guide catheter including a distal end at least in which a guide wire is configured to be arranged, and wherein the stent and the pusher tube are movable distally together through a distal movement of the pusher tube with respect to the guide catheter;
a linear member including a proximal end portion configured to be located at the proximal side of the stent and a distal end portion configured to be located within the lumen; and
an engagement member provided at a distal end of the linear member, configured to be engaged with the engagement receiving portion through inserting the guide catheter into the lumen so as to push the engagement member toward the engagement receiving portion by a faced portion of the guide catheter, facing the engagement receiving portion, and holding the engagement member between the faced portion and the engagement receiving portion, and is switchable through an axial movement of the guide catheter with respect to the stent from a first state where the engagement member is engaged with the engagement receiving portion such that the stent and the pusher tube are movable proximally together through a proximal movement of the linear member with respect to the guide catheter to a second state where the engagement member is disengaged from the engagement receiving portion such that the stent and the pusher tube are separable in the axial direction with respect to each other.

2. A stent delivery device according to claim 1, wherein the stent has an engagement depression formed in an inner wall thereof and engageable with the engagement member, and in the first state, the engagement member is engaged with the engagement depression and a circumferential wall of the guide catheter inserted in the stent.

3. A stent delivery device according to claim 1, wherein the proximal end portion of the linear member is fixed to the pusher tube such that the stent and the pusher tube are movable proximally together through a proximal movement of the pusher tube with respect to the guide catheter.

4. A stent delivery device according to claim 1, wherein the circumferential wall of the guide catheter has an opening into which the engagement member puts, and the second state is established when the engagement member puts into the opening.

5. A stent delivery device according to claim 1, wherein the engagement receiving portion includes an engagement hole.

6. A stent delivery device according to claim 1, wherein the guide catheter is located on a distal end side of the pusher tube, and the guide catheter has a proximal end portion connected to a distal end portion of a pull wire inserted in the pusher tube, the pull wire inside the pusher tube being movable forward and backward.

7. A stent delivery device comprising:
a stent configured to be placed in a body cavity and including a lumen and an engagement receiving portion;
a pusher tube configured to be located at a proximal side of the stent;
an elongated guide member configured to be inserted through the stent and the pusher tube such that the guide member is movable in an axial direction of the guide member with respect to the stent and the pusher tube, and wherein the stent and the pusher tube are movable distally together through a distal movement of the pusher tube with respect to the guide member;
a linear member including a proximal end portion configured to be located at the proximal side of the stent and a distal end portion configured to be located within the lumen; and
an engagement member provided at a distal end of the linear member, configured to be engaged with the engagement receiving portion through inserting the guide member into the lumen so as to push the engagement member toward the engagement receiving portion by a faced portion of the guide member, facing the engagement receiving portion, and holding the engagement member between the faced portion and the engagement receiving portion, and is switchable through an axial movement of the guide member with respect to the stent from a first state where the engagement member is engaged with the engagement receiving portion such that the stent and the pusher tube are movable proximally together through a proximal movement of the linear member with respect to the guide member to a second state where the engagement member is disengaged from the engagement receiving portion such that the stent and the pusher tube are separatable in the axial direction with respect to each other.

8. A stent delivery device according to claim 7, wherein in the first state, the engagement member is engaged with a circumferential wall of the guide member inserted in the stent and an inner surface of the stent, the engagement member has a distal end portion configured to hold a distal end portion of the stent and a proximal end portion configured to hold a proximal end portion of the stent.

* * * * *